Figure 1:
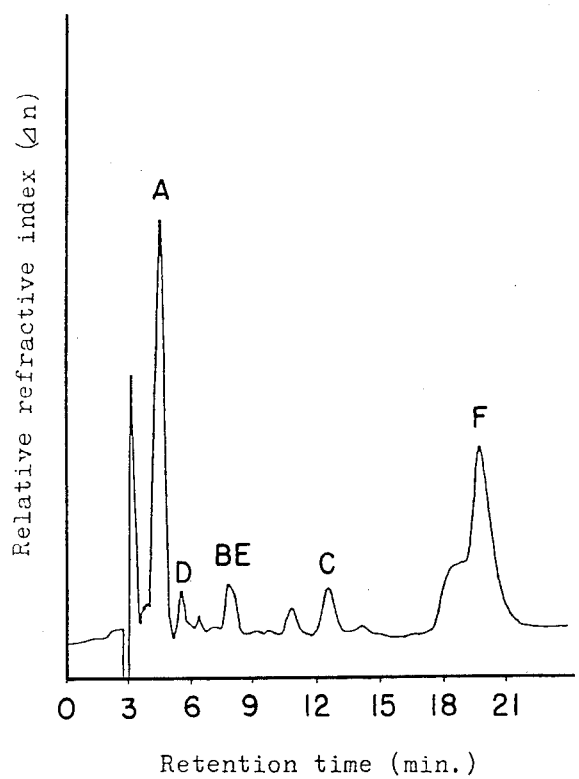

United States Patent [19]

Bunno et al.

[11] Patent Number: 4,520,102
[45] Date of Patent: May 28, 1985

[54] MICROBIAL PROCESS FOR PRODUCING 12α-HYDROXYPREGNA-1,4-DIEN-3-ONE-20α-CARBOXYLIC ACID

[75] Inventors: Masayasu Bunno, Nagareyama; Tsutomu Sugiura, Kurashiki; Masao Tsuji, Kurashiki; Hidemi Harada, Kurashiki; Yoshihiro Ichihara, Kurashiki, all of Japan

[73] Assignee: Kuraray Co., Ltd., Kurashiki, Japan

[21] Appl. No.: 434,560

[22] Filed: Oct. 15, 1982

[30] Foreign Application Priority Data

Oct. 20, 1981 [JP] Japan .................................. 56-168276
Feb. 5, 1982 [JP] Japan .................................. 57-17866

[51] Int. Cl.³ .................... C12P 33/02; C12N 15/00; C12R 1/05; C12R 1/38
[52] U.S. Cl. .................... 435/61; 435/172.1; 435/874; 435/829
[58] Field of Search ...................... 435/61, 172.1, 874, 435/829

[56] References Cited

U.S. PATENT DOCUMENTS 3,022,226  2/1962  Ross et al. ............................ 435/61

OTHER PUBLICATIONS

Barnes et al., Tetrahedron, vol. 32, pp. 89–93, 1976.

*Primary Examiner*—Alvin E. Tanenholtz
*Attorney, Agent, or Firm*—Wegner & Bretschneider

[57] ABSTRACT

A microbial process for producing 12α-hydroxypregna-1,4-dien-3-one-20α-carboxylic acid or a salt thereof which comprises cultivating a microbe of the species *Pseudomonas arvilla* or the genus Alcaligenes, e.g. *Alcaligenes faecalis*, which is capable of producing 12α-hydroxypregna-1,4-dien-3-one-20α-carboxylic acid or a salt thereof by utilizing deoxycholic acid or a salt thereof as a substrate, in a culture medium containing the substrate and collecting the resulting compound.

4 Claims, 1 Drawing Figure

MICROBIAL PROCESS FOR PRODUCING 12α-HYDROXYPREGNA-1,4-DIEN-3-ONE-20α-CARBOXYLIC ACID

The present invention relates to a microbial process for producing 12α-hydroxypregna-1,4-dien-3-one-20α-carboxylic acid or a salt thereof from deoxycholic acid or a salt thereof. More particularly, according to the present invention, 12α-hydroxypregna-1,4-dien-3-one-20α-carboxylic acid or a salt thereof can be produced in a high yield by cultivating a certain microbe of the species *Pseudomonas arvilla* or the genus Alcaligenes in a culture medium containing deoxycholic acid or a salt thereof as a substrate.

12α-Hydroxypregna-1,4-dien-3-one-20α-carboxylic acid can be used as a starting material for the synthesis of various steroid hormones.

Several microbial processes for producing 12α-hydroxypregna-1,4-dien-3-one-20α-carboxylic acid have been known heretofore in the prior art. For example, P. J. Barnes et al. disclose a process using Pseudomonas sp. NCIB 10590 strain [J. Chem. Soc. Chem. Commun. (1974), pp 115–116 and Tetrahedron, 32, pp 89–93 (1976)]. In this process, Pseudomonas sp. NCIB 10590 strain is cultivated in a mineral medium containing 0.1% of sodium deoxycholate as a substrate under an aerobic condition to produce as major products 12α-hydroxypregna-1,4-dien-3-one-20α-carboxylic acid and 12β-hydroxyandrosta-1,4-dien-3,17-dione together with as minor products 12α-hydroxyandrosta-1,4-dien-3,17-dione, 12β-hydroxy-4-androsten-3,17-dione and 12ξ,17ξdihydroxy-4-androsten-3-one. However, this process is impractical because of its low yield of 12α-hydroxypregna-1,4-dien-3-one-20α-carboxylic acid (less than 7%), production of a large amount of androstane by-products and the low concentration of the substrate. Besides, as to Pseudomonas sp. NCIB 10590 strain used in this process, there is no disclosure other than that the strain has been isolated from animal faeces and belongs to the genus Pseudomonas.

Further, M. E. Tenneson et al. disclose a process for producing 12α-hydroxypregna-1,4-dien-3-one-20α-carboxylic acid and 12β-hydroxyandrosta-1,4-dien-3,17-dione from deoxycholic acid by using an anaerobic strain of *Escherichia coli* [Biochem. Soc. Trans., 5, pp 1758–1760 (1977)]. R. W. Owen et al. disclose a process for producing 12α-hydroxypregna-1,4-dien-3-one-20α-carboxylic acid, 12β-hydroxyandrosta-1,4-dien-3,17-dione, 12α-hydroxyandrosta-1,4-dien-3,17-dione and 12β-hydroxy-4-androsten-3,17-dione from deoxycholic acid by using *Bacteroides fragilis* XF 23 strain or *Bacteroides fragilis* subsp. thetaiotaomicron E 59 strain [Biochem. Soc. Trans., 5, pp 1711–1713 (1977)]. However, in these processes, anaerobic strains are used and hence, where these processes are applied to the industrial production of 12α-hydroxypregna-1,4-dien-3-one-20α-carboxylic acid, there are such problems that a low concentration of the substrate and a long-term cultivation are unavoidable and a yield of the product is low.

The present inventors have intensively searched and studied in order to obtain a microbe which is useful in the industrial production of 12α-hydroxypregna-1,4-dien-3-one-20α-carboxylic acid or a salt thereof by utilizing deoxycholic acid or a salt thereof as a substrate. As the result, it has been found that a certain microbe of the species *Pseudomonas arvilla* or the genus Alcaligenes can produce 12α-hydroxypregna-1,4-dien-3-one-20α-carboxylic acid or a salt thereof from deoxycholic acid or a salt thereof in a high selectivity and yield.

The main object of the present invention is to provide a microbial process for producing 12α-hydroxypregna-1,4-dien-3-one-20α-carboxylic acid or a salt thereof which is suitable for the industrial production of said compound. This object as well as other objects and advantages of the present invention will become apparent to those skilled in the art from the following description.

According to the present invention, there is provided a microbial process for producing 12α-hydroxypregna-1,4-dien-3-one-20α-carboxylic acid or a salt thereof which comprises cultivating a microbe of the species *Pseudomonas arvilla* or the genus Alcaligenes, which is capable of producing 12α-hydroxypregna-1,4-dien-3-one-20α-carboxylic acid or a salt thereof by utilizing deoxycholic acid or a salt thereof as a substrate, in a culture medium containing the substrate and collecting the resulting compound.

The microbes to be used in the present invention may be wild-type strains of the species *Pseudomonas arvilla* or the genus Alcaligenes or mutants thereof obtained by natural mutation or a conventional mutagenic treatment such as X-ray irradiation, ultraviolet irradiation, treatment with a chemical mutagen such as N-methyl-N'-nitro-N-nitrosoguanidine, 4-nitroquinoline-N-oxide, acriflavine or ethylmethane sulfonate) or combination thereof and the like.

Among the microbes being capable of producing 12α-hydroxypregna-1,4-dien-3-one-20α-carboxylic acid or a salt thereof by utilizing deoxycholic acid or a salt thereof as a substrate obtained by the present inventors, the representatives have been deposited with Fermentation Research Institute, Agency of Industrial Science and Technology, Japan (hereinafter, referred to as FERM). They are *Pseudomonas arvilla* D-235 strain (FERM BP-181), *Alcaligenes faecalis* D4020 strain (FERM BP-182) and *Alcaligenes faecalis* D4020-H405 strain (FERM BP-183). *Pseudomonas arvilla* D-235 strain and *Alcaligenes faecalis* D4020 strain are wild-type strains isolated from soil and *Alcaligenes faecalis* D4020-H405 strain is a mutant of *Alcaligenes faecalis* D4020 strain. Besides, *Pseudomonas arvilla* D-235 strain is differentiated from Pseudomonas sp. NCIB 10590 strain used in the above process of P. J. Barnes et al. because *Pseudomonas arvilla* D-235 strain hardly produces 12β-hydroxyandrosta-1,4-dien-3,17-dione at any stage of cultivation in a culture medium containing deoxycholic acid or a salt thereof.

The morphological, cultural and physiological characteristics of these strains are shown in Table 1.

TABLE 1

| Characteristics | Ps. arvilla D-235 | A. faecalis D4020 | A. faecalis D4020-H405 |
|---|---|---|---|
| Microscopic observation | | | |
| Form | rods | rods | rods |
| Size (μ) | 0.3–0.7 × 1.5–2.4 | 0.5 × 1.2–1.7 | 0.5 × 1.0–1.8 |
| Flagellum | polar flagella | peritrichous | peritrichous |

TABLE 1-continued

| Characteristics | Ps. arvilla D-235 | A. faecalis D4020 | A. faecalis D4020-H405 | | | |
|---|---|---|---|---|---|---|
| | (2–4, multi-trichous) | flagella | flagella | | | |
| Spore | nil | nil | nil | | | |
| Gram stain | negative | negative | negative | | | |
| Acid fast stain | nil | nil | nil | | | |
| Cultural observation | | | | | | |
| Nitrient (Bouillon) agar plate culture | circular, flat, entire, white glistening, smooth | circular, opaque, convex | circular, opaque, convex | | | |
| Nutrient (Bouillon) agar slant culture | spreading, milk-white, smooth | moderate growth, filiform, pigments not produced | moderate growth, filiform, pigments not produced | | | |
| Nutrient broth (Bouillon) culture | pellicle, precipitation | moderate turbidity, pellicle | moderate turbidity | | | |
| Potato-glucose agar[1] slant culture | echinurate, white, opalescent | not examined | not examined | | | |
| Growth temperature | growth at 37° C. | growth at 37° C., inferior growth at 41° C. | growth at 37° C., inferior growth at 41° C. | | | |
| Gelatin stab | no liquefaction | no liquefaction | no liquefaction | | | |
| Litmus milk | litmus not reduced, milk coagulated and not peptonized | alkaline, milk unchanged | alkaline, milk unchanged | | | |
| BCP milk | initially alkaline, becoming acidic after 1 week cultivation | alkaline, milk unchanged | alkaline, milk unchanged | | | |
| Physiological character[2] | | | | | | |
| Nitrate reduction | − | + | + | | | |
| Denitrification | − | − | − | | | |
| Methyl red test | − | − | − | | | |
| Voges-Proskauer test | − | − | − | | | |
| Indole production | − | − | − | | | |
| H₂S production | − | − | − | | | |
| Starch hydrolysis | − | − | − | | | |
| Citrate utilization | + | + | + | | | |
| Succinate utilization | + | not examined | not examined | | | |
| Glutamate utilization | + | not examined | not examined | | | |
| p-Hydroxybenzoate utilization | + | not examined | not examined | | | |
| Assimilation of inorganic nitrogen sources | + | + | + | | | |
| Urease | − | ± | ± | | | |
| Oxidase | + | + | + | | | |
| Catalase | + | + | + | | | |
| Require of oxygen | aerobic | aerobic | aerobic | | | |
| Oxidation/Fermentation test | oxidative | oxidative | oxidative | | | |
| Production of acids and[3] gases from carbohydrates | acids | gases | acids | gases | acids | gases |
| L-Arabinose | + | − | + | − | + | − |
| D-Xylose | + | − | + | − | + | − |
| D-Glucose | + | − | + | − | + | − |
| D-Mannose | + | − | + | − | + | − |
| D-Fructose | − | − | − | − | − | − |
| D-Galactose | + | − | + | − | + | − |
| Maltose | + | − | − | − | − | − |
| Sucrose | + | − | − | − | − | − |
| Lactose | + | − | − | − | − | − |
| Trehalose | − | − | − | − | − | − |
| D-Sorbitol | − | − | − | − | − | − |
| D-Mannitol | − | − | − | − | − | − |
| Inositol | − | − | − | − | − | − |
| Glycerol | − | − | − | − | − | − |
| Starch | − | − | − | − | − | − |

Remarks:
[1]The culture medium containing potato extract (4.0 g/l), glucose (20.0 g/l) and agar (15.0 g/l).
[2]The symbols used in Physiological character have the following meaning.
+: The strain has the corresponding character or produces the corresponding product.
±: It is difficult to determine whether the strain has the corresponding character or produces the corresponding product or not.
−: The strain does not have the corresponding character or does not produce the corresponding product.
[3]By using Hugh and Leifson medium in which each of the carbohydrates shown in Table 1 was substituted for the carbon source thereof, production of acids and gases by the strain was observed.
+: An acid or a gas is produced.
±: It is difficult to determine whether an acid or a gas is produced or not.
−: An acid or a gas is not produced.

On the basis of these morphological, cultural and physiological characteristics, the classification of the strains has been determined according to Bergey's Manual of Determinative Bacteriology 7th and 8th Editions.

It is determined that *Pseudomonas arvilla* D-235 strain is a microbe of the genus Pseudomonas in view of its microscopic observation such as rod-form, polar flagella and negative in gram stain as well as its physiological character such as positive in both oxidase and catalase reactions and oxidative in Oxidation/Fermentation test. Further, it is determined that *Pseudomonas arvilla* D-235 strain is a microbe of the species *Pseudomonas arvilla* in view of its size (0.3–0.7×1.5–2.4μ); white, flat and glistening colonies on agar plate; no production of pigments; no liquefaction of gelatin stab; no reduction of nitrate and acid-production from glucose.

It is also determined that *Alcaligenes faecalis* D4020 strain is a microbe of the genus Alcaligenes in view of its microscopic observation such as rod-form, peritrichous flagella and negative in gram stain as well as its physiological character such as positive in both oxidase and catalase reactions and oxidative in Oxidation/Fermentation test. Further, it is determined that *Alcaligenes faecalis* D4020 strain is a microbe of the species *Alcaligenes faecalis* in view of no liquefaction of gelatin stab, behavior in cultivation using litmus milk and BCP milk (milk being unchanged except becoming alkaline) and no denitrification. It is determined that *Alcaligenes faecalis* D4020-H405 strain is a microbe of the species *Alcaligenes faecalis* because, in general, a mutant is classified into the same species of its parent strain.

The process of the present invention is carried out by cultivating a microbe of the species *Pseudomonas arvilla* or the genus Alcaligenes, which is capable of producing 12α-hydroxypregna-1,4-dien-3-one-20α-carboxylic acid or a salt thereof by utilizing deoxycholic acid or a salt thereof as a substrate, in a culture medium containing the substrate and collecting the resulting compound.

In the present invention, deoxycholic acid per se can be used as a substrate. There can be also used an alkali metal salt of deoxycholic acid such as sodium deoxycholate, potassium deoxycholate or the like or an alkaline earth metal salt of deoxycholic acid such as calcium deoxycholate, magnesium deoxycholate or the like, preferably an alkali metal salt. When a deoxycholate is used, it is dissolved in a water to prepare an aqueous solution containing the deoxycholate in a predetermined concentration. Alternatively, a certain amount of an alkali metal compound or an alkaline earth metal compound which forms a salt with deoxycholic acid may previously be dissolved in water and added thereto deoxycholic acid to obtain an aqueous solution containing a deoxycholate in a predetermined concentration.

In general, concentration of the substrate in a culture medium may be varied widely in a range of from about 1 to 200 g/l as deoxycholic acid. However, in view of a yield of the desired product, conditions for cultivation and economic efficiency such as operability, workability and the like, it is preferable to use the substrate in a concentration of about 10 to 100 g/l as deoxycholic acid.

Cultivation can be carried out according to a known method under an aerobic condition and, usually, a shaking or submerged culture using a liquid medium is employed.

As a medium, there can be used one containing nutrients which can be assimilated by the microbe to be used. The medium can contain deoxycholic acid or a salt thereof as the sole carbon source and, optionally, it can contain an additional carbon source. In case of cultivating a microbe of the species *Pseudomonas arvilla*, as said additional carbon source there can be used a pentose (e.g. arabinose, etc.), a hexose (e.g. glucose, mannose, fructose, galactose, etc.), a disaccharide (e.g. sucrose, maltose, etc.), a starch decomposition product (e.g. dextrin, etc.), a sugar alcohol (e.g. sorbitol, etc.), a polyvalent alcohol (e.g. glycerol, etc.), polypeptone, peptone, meat extract, malt extract, corn steep liquor, yeast extract, an amino acid, an organic acid or a mixture thereof. And in case of cultivating a microbe of the genus Alcaligenes, as said additional carbon source there can be used preferably a hexose (e.g. glucose, etc.), a polyvalent alcohol (e.g. glycerol, etc.), peptone, meat extract, yeast extract or a mixture thereof. Usually, the additional carbon source can be added to the medium in a concentration of about 0.1 to 20 g/l. Further, as a nitrogen souce, there can be used an inorganic nitrogen source such as ammonium sulfate, ammonium chloride, ammonium phosphate, ammonium nitrate, sodium nitrate, potassium nitrate, etc.; an organic nitrogen source such as polypeptone, peptone, meat extract, etc.; or a mixture thereof. Usually, the nitrogen source can be added to the medium in a concentration of about 0.5 to 5 g/l. In addition, an inorganic salt such as dipotassium hydrogen phosphate, potassium dihydrogen phosphate, magnesium sulfate, manganese sulfate, zinc sulfate, cobalt chloride, sodium molybdate, cupric sulfate, calcium chloride, sodium chloride, etc. or a mixture thereof can be added to the medium.

A condition for cultivation is not limited to a specific one but, usually, cultivation can be carried out in a shaking or submerged culture of pH about 7 to 9 at about 25° to 35° C. for about 10 hours to 7 days to produce and accumulate 12α-hydroxypregna-1,4-dien-3-one-20α-carboxylic acid or a salt thereof in the medium.

12α-Hydroxypregna-1,4-dien-3-one-20α-carboxylic acid or a salt thereof thus accumulated in the medium can be collected by separating it from the medium according to a known method. For example, microbial cells and other insoluble materials in the medium are removed from the medium by filtration, centrifugation and the like. Then, the resulting filtrate or supernatant is acidified by addition of an acid such as hydrochloric acid, sulfuric acid, etc. and extracted with an organic solvent which can dissolve the above desired carboxylic acid and form a phase separated out from water (e.g. ethyl acetate, chloroform, a mixture of chloroform and methanol, etc.). The solvent is distilled off from the resulting extract to obtain the desired 12α-hydroxypregna-1,4-dien-3-one-20α-carboxylic acid. This extraction can be effected not only on the filtrate or supernatant but also on the medium itself and can be effected without addition of any acid. Further, when the filtrate or supernatant is acidified, 12α-hydroxypregna-1,4-dien-3-one-20α-carboxylic acid is precipitated and the precipitate as such can be separated by filtration, centrifugation and the like to obtain the desired product.

The extract or precipitated thus obtained can be purified, for example, by subjecting it to chromatography on a silica gel column and eluting with a mixture of chloroform and ethanol or by simply recrystallizing from a solvent such as water-methanol.

12α-hydroxypregna-1,4-dien-3-one-20α-carboxylic acid obtained in the present invention can be converted into 12α-hydroxypregna-1,4-dien-3,20-dione, which has been used as a starting material for the synthesis of various steroid hormones such as predonisone, by decarboxylating the carboxylic acid group at 20-position thereof according to the same method as described by H. Ruschig et al. [Chem. Ber., 88, p 883 (1955)].

The following examples further illustrate the present invention in detail but are not to be construed to limit the scope thereof.

Preparation of mutant

One loopful of *Alcaligenes faecalis* D4020 strain cultivated on a slant medium (medium A: deoxycholic acid 0.5%, NaOH 0.05%, peptone 0.5%, yeast extract 0.5%, NaCl 0.5% and agar 1.5%) was inoculated into a medium (10 ml, medium B: deoxycholic acid 2%, NaOH 0.2%, $NH_4NO_3$ 0.2%, $KH_2PO_4$ 0.1%, $K_2HPO_4$ 0.6%, $MgSO_4.7H_2O$ 0.02% and yeast extract 0.02%) in a test tube (200 mm $\times$ 21 mm in diameter), and incubated with shaking at 30° C. for 8 to 10 hours. The resulting culture (0.3 ml) was added to a medium (10 ml, medium C: deoxycholic acid 0.5%, NaOH 0.05%, glucose 0.1%, $NH_4NO_3$ 0.2%, $KH_2PO_4$ 0.1%, $K_2HPO_4$ 0.6%, $MgSO_4.7H_2O$ 0.02% and yeast extract 0.02%) in a test tube (200 mm $\times$ 21 mm in diameter), and incubated at 30° C. for 10 to 15 hours. The microbial cells in a log phase were collected by a membrane filter (pore size 0.45μ) under an aseptic condition, washed with 0.1M phosphate buffer (pH 7.0, 20 ml) and suspended in the same buffer (25 ml).

Mutagenic treatment was carried out by adding N-methyl-N'-nitro-N-nitrosoguanidine in a final concentration of 20 μg/ml to the above-prepared cell suspension and incubating the mixture with shaking at 30° C. for 10 to 15 minutes.

The cells thus treated were collected by a membrane filter (pore size 0.45μ), washed with 0.1M phosphate buffer (pH 7.0, 20 ml) and suspended in the same buffer (20 ml). The resulting cell suspension was diluted with a sterilized physiological saline solution and spread on agar plates (medium D: deoxycholic acid 0.5%, NaOH 0.05%, $NH_4NO_3$ 0.2%, $KH_2PO_4$ 0.1%, $K_2HPO_4$ 0.6%, $MgSO_4.7H_2O$ 0.02%, yeast extract 0.02% and agar 1.5%) so as to from 500 to 1,000 colonies per one plate. The plates were incubated at 30° C. for 3 to 4 days.

Among the colonies thus formed, a pin point colony was isolated by cultivating it on a slant of the medium A and one loopful of the culture was inoculated into a medium (10 ml, medium E: deoxycholic acid 0.2%, NaOH 0.02%, glucose 0.1%, $NH_4NO_3$ 0.2%, $KH_2PO_4$ 0.1%, $K_2HPO_4$ 0.6%, $MgSO_4.7H_2O$ 0.02% and yeast extract 0.02%) in a test tube (200 mm $\times$ 21 mm in diameter), and incubated with shaking at 30° C. for 24 hours.

Upon examining products accumulated in the medium E by thin layer chromatography, a microbe which selectively produced 12α-hydroxypregna-1,4-dien-3-one-20α-carboxylic acid or its salt was found and named *Alcaligenes faecalis* D4020-H405 strain.

EXAMPLE 1

*Pseudomonas arvilla* D-235 strain was cultivated as follows:
Composition of culture medium

| | |
|---|---|
| Deoxycholic acid | 5.0 g |
| Ammonium nitrate | 0.2 g |
| Potassium dihydrogen phosphate | 0.1 g |
| Dipotassium hydrogen phosphate | 0.25 g |
| Magnesium sulfate heptahydrate | 0.02 g |
| Yeast extract | 0.01 g |
| Sodium hydroxide | 0.5 g |
| Tap water | to 100 ml |

The above ingredients were admixed to obtain a culture medium (pH 7.2, 100 ml). The medium was placed in a Sakaguchi flask (volume 500 ml) and autoclaved at 120° C. for 15 minutes. To the flask, there was added seed culture (10 ml) which was obtained by previously cultivating the strain in the same medium with shaking at 30° C. for 2 days. The flask was incubated on a shaker at 30° C. for 5 days.

After completion of cultivation, the culture medium was collected and centrifuged to remove microbial cells. The resulting supernatant was acidified by addition of hydrochloric acid to adjust pH thereof to 2. The supernatant was extracted with a mixture (300 ml) of chloroform and methanol (2:1, v/v). Chloroform-methanol was distilled off from the extract by a rotary evaporator to obtain a mixture (2.9 g) of oxidation products of deoxycholic acid and unreacted deoxycholic acid.

A small portion of the mixture was dissolved in methanol in the concentration of 1%. The solution (20 μl) was injected to a high-performance liquid chromatography apparatus equipped with a μBondapak C-18 column (HLC-GPC-244 type manufactured by Waters Associates in U.S.A.). The column was eluted with water-methanol (25:75, v/v, pH 4.0) at the rate of 1 ml/min. and refractive index of the eluate was measured.

The accompanying FIGURE 1 shows the resulting chromatogram. The peaks, A, B, C, D, E and F in FIGURE 1 correspond to those of the reference standards of 12α-hydroxypregna-1,4-dien-3-one-20α-carboxylic acid, 12α-hydroxy-3-keto-4-cholenic acid, 12α-hydroxy-3-keto-5β-cholanic acid, 12α-hydroxy-3-keto-chola-1,4-dienic acid, 12α-hydroxy-3-keto-5β-pregnan-20α-carboxylic acid and deoxycholic acid, respectively.

The above mixture (2.8 g) was dissolved in a small amount of chloroform-ethanol (99:1, v/v) and absorbed on a silica gel (50 g) column and the column was washed with chloroform-ethanol (99:1, v/v, 500 ml) and eluted with chloroform-ethanol (97:3, v/v, 1 liter). Chloroform-ethanol was distilled off from the eluate by a rotary evaporator to obtain a mixture of oxidation products of deoxycholic acid (310 mg). Further, the above column was eluted with chloroform-ethanol (95:5, v/v, 500 ml) and each 10 ml portions of the eluate was collected in a fraction tube. The fractions which showed a single spot by thin layer chromatography were combined and the solvent was distilled off to obtain a solid (650 mg). This solid was recrystallized from ethyl acetate to obtain 12α-hydroxypregna-1,4-dien-3-one-20α-carboxylic acid (450 mg). The above column was further eluted with chloroform-ethanol (90:10, v/v, 200 ml) and unreacted deoxycholic acid (1.2 g) was recovered from the eluate.

The above mixture of oxidation products of deoxycholic acid (310 mg) resulted from the eluate of chloroform-ethanol (97:3, v/v) was dissolved in a small amount of chloroform-ethanol (99:1, v/v) and the solution was absorbed on silica gel (20 g) column. The column was eluted with chloroform-ethanol (98:2, v/v) and then with chloroform-ethanol (97:3, v/v). Each 10 ml portions of the eluate was collected in a fraction tube. Fractions which showed a corresponding single spot by thin layer chromatography were combined and the solvent was distilled off by a rotary evaporator. As the results, 12α-hydroxy-3-keto-5β-cholanic acid (80 mg) was obtained from the first half of the fractions eluted with chloroform-ethanol (98:2, v/v) and 12α-hydroxy-3-keto-4-cholenic acid (10 mg) was obtained from the latter half thereof. 12α-Hydroxy-3-keto-5β-pregnan-20α-carboxylic acid (5 mg) was obtained from the first half of the fractions eluted with chloroform-ethanol (97:3, v/v) and 12α-hydroxy-3-keto-chola-1,4-dienic acid (10 mg) was obtained from the latter half thereof.

Each compound thus obtained was identified as follows:

12α-hydroxypregna-1,4-dien-3-one-20α-carboxylic acid

Mass spectrum: m/z=358 [M]+; 340 [M-H$_2$O]+; and 322 [M-2H$_2$O]+. The presence of 3-keto-1,4-dien was confirmed by m/z=122 and the presence of —CH(CH$_3$)COOH was confirmed by m/z=74.

NMR spectrum (90 MHz): $\delta_{HMS}^{DMSO-d6}$=0.65 (3H,s) 18-CH$_3$; 1.05 (3H, d) 21-CH$_3$; 1.13 (3H, s) 19-CH$_3$; 3.74 (1H, t, J=3 Hz) 12β-H; 4.33 (1H, d) 12α-OH; 5.93 (1H, s) 4-H; 6.06 (1H, d, J=10 Hz) 2-H; and 7.08 (1H, d, J=10 Hz) 1-H.

Melting point of methyl ester: 236° C.

12α-hydroxy-3-keto-4-cholenic acid

Mass spectrum: m/z=388 [M]+; 370 [M—H$_2$O]+; and 355 [M—H$_2$O—CH$_3$]+. The presence of 3-keto-4-en was confirmed by m/z=124 and the presence of —CH$_2$COOH was confirmed by m/z=60.

NMR spectrum (90 MHz): $\delta_{HMS}^{DMSO-d6}$=0.60 (3H, s) 18-CH$_3$; 0.86 (3H, d) 21-CH$_3$; 1.07 (3H, s) 19-CH$_3$; 3.75 (1H, t, J=3 Hz) 12β-H; and 5.56 (1H, s) 4-H.

12α-hydroxy-3-keto-5β-cholanic acid

Mass spectrum: m/z=390 [M]+; 372 [M—H$_2$O(9 +; 354 [M—2H$_2$O]+; and 339 [M—2H$_2$O—CH$_3$]+. The presence of —CH$_2$COOH was confirmed by m/z=60.

NMR spectrum (90 MHz): $\delta_{HMS}^{DMSO-d6}$=0.57 (3H, s) 18-CH$_3$; 0.83 (3H, d) 21-CH$_3$; 0.89 (3H, s) 19-CH$_3$; and 3.76 (1H, t, J=3 Hz) 12β-H.

12α-hydroxy-3-keto-chola-1,4-dienic acid

Mass spectrum: m/z=386 [M]+; 368 [M-H$_2$O]+; and 353 [M—H$_2$O—CH$_3$]+. The presence of 3-keto-1,4-dien was confirmed by m/z=122 and the presence of —CH$_2$COOH was confirmed by m/z=60.

NMR spectrum (90 MHz): $\delta_{HMS}^{DMSO-d6}$=0.63 (3H, s) 18-CH$_3$; 0.85 (3H, d) 21-CH$_3$; 1.11 (3H, s) 19-CH$_3$; 3.78 (1H, t, J=3 Hz) 12β-H; 5.91 (1H, s) 4-H; 6.05 (1H, d, J=10 Hz) 2-H; and 7.08 (1H, d, J=10 Hz) 1-H.

12α-hydroxy-3-keto-5β-pregnan-20α-carboxylic acid

Mass spectrum: m/z=362 [M]+; 344 [M—H$_2$O]+; and 326 [M—2H$_2$O]+. The presence of —CH(CH$_3$)COOH was confirmed by m/z=74.

NMR spectrum (90 MHz): $\delta_{HMS}^{DMSO-d6}$=0.63 (3H, s) 18-CH$_3$; 1.07 (6H, m) 19-CH$_3$ and 21-CH$_3$; 3.75 (1H, t, J=3 Hz) 12β-H; and 4.28 (1H, d) 12α-OH.

The area ratio of each peak of the chromatogram in FIG. 1 was measured by using a planimeter (Shimadzu Chromatopack C-RIA manufactured by Shimadzu Corporation in Japan) and the yield of the products and the amount of deoxycholic acid which remained without being converted were calculated based on the area ratio. The results are shown in Table 2.

TABLE 2

| Compounds | Area ratio (%) | Yield or amount (mg) |
|---|---|---|
| 12α-hydroxypregna-1,4-dien-3-one-20α-carboxylic acid (peak A) | 38.1 | 1,105 |
| a mixture of 12α-hydroxy-3-keto-4-chlenic acid and 12α-hydroxy-3-keto-5β-pregnan-20α-carboxylic acid (peaks B and E) | 4.8 | 139 |
| 12α-hydroxy-3-keto-5β-cholanic acid (peak C) | 5.0 | 145 |
| 12α-hydroxy-3-keto-chola-1,4-dienic acid (peak D) | 3.1 | 89 |
| other oxidation products of deoxycholic acid | 5.0 | 146 |
| deoxycholic acid (peak F) | 44.0 | 1,276 |

EXAMPLE 2

Pseudomonas arvilla D-235 strain was cultivated under the same condition as described in Example 1 except that deoxycholic acid (2.0 g) and sodium hydroxide (0.2 g) were substituted for deoxycholic acid (5.0 g) and sodium hydroxide (0.5 g) and the medium was worked up according to the same procedure as in Example 1 to obtain a mixture (420 mg) of oxidation products of deoxycholic acid and unreacted deoxycholic acid.

A small portion of the mixture was dissolved in methanol in the concentration of 1%. The solution (20 μl) was injected to a high-performance liquid chromatography apparatus equipped with a μBondapak C-18 column (HLC-GPC-244 type manufactured by Waters Associates in U.S.A.). The column was eluted with water-methanol (25:75, v/v, pH 4.0) at the rate of 1 ml/min. and refractive index of the eluate was measured. According to the same procedure as in Example 1, the yield of the products and the amount of deoxycholic acid which remained without being converted were calculated. The results are shown in Table 3.

TABLE 3

| Compounds | Yield or amount (mg) |
|---|---|
| 12α-hydroxypregna-1,4-dien-3-one-20α-carboxylic acid | 349 |
| a mixture of 12α-hydroxy-3-keto-4-cholenic acid and 12α-hydroxy-3-keto-5β-pregnan-20α-carboxylic acid | 9 |
| 12α-hydroxy-3-keto-5β-cholanic acid | 2 |
| 12α-hydroxy-3-keto-chola-1,4-dienic acid | 12 |
| other oxidation products of deoxycholic acid | 46 |
| deoxycholic acid | 2 |

EXAMPLE 3

Pseudomonas arvilla D-235 strain was cultivated as follows:

Composition of culture medium

| Deoxycholic acid | 0.5 g |
| Glucose | 0.05 g |
| Ammonium nitrate | 0.02 g |
| Potassium dihydrogen phosphate | 0.01 g |
| Dipotassium hydrogen phosphate | 0.03 g |
| Magnesium sulfate heptahydrate | 0.002 g |
| Yeast extract | 0.002 g |
| Tap water | to 10 ml |

The medium was placed in a test tube (200 mm×21 mm in diameter) and autoclaved at 120° C. for 15 minutes. One loopful of seed culture which was obtained by previously cultivating the strain on a slant (prepared by an aqueous solution containing deoxycholic acid 1%, peptone 0.5%, meat extract 0.5%, NaCl 0.5%, agar 1.5% and NaOH 0.1%) at 30° C. for 1 day was inoculated in the above-prepared culture medium and incubated with shaking at 30° C. for 6 days.

After completion of cultivation, oxidation products of deoxycholic acid and unreacted deoxycholic acid were extracted from the culture medium with chloroform (200 ml). The extract was separated and chloroform was distilled off from the extract by a rotary evaporator to obtain a mixture (390 mg) of the oxidation products of deoxycholic acid and unreacted deoxycholic acid.

A small portion of the mixture was dissolved in methanol in the concentration of 2%. The solution (20 μl) was injected to a high-performance liquid chromastography apparatus equipped with μBondapak C-18 column (HLC-GPC-244 type manufactured by Waters Associates in U.S.A.). The column was eluted with water-methanol (25:75, v/v, pH 4.0) at the rate of 1 ml/min. and refractive index of the eluate was measured. When the yield of the products and the amount of deoxycholic acid which remained without being converted were calculated according to the same procedure as in Example 1, the yields of 12α-hydroxypregna-1,4-dien-3-one-20α-carboxylic acid and other oxidation products of deoxycholic acid were 60 mg and 20 mg, respectively and the amount of unreacted deoxycholic acid was 310 mg.

EXAMPLE 4

*Alcaligenes faecalis* D4020 strain was cultivated as follows:

Composition of culture medium

| | |
|---|---|
| Deoxycholic acid | 2.0 g |
| Ammonium nitrate | 0.2 g |
| Potassium dihydrogen phosphate | 0.12 g |
| Dipotassium hydrogen phosphate | 0.61 g |
| Magnesium sulfate heptahydrate | 0.02 g |
| Yeast extract | 0.02 g |
| Sodium hydroxide | 0.2 g |
| Tap water | to 110 ml |

The above ingredients were admixed to obtain a culture medium (pH 8.4, 100 ml). The medium was placed in a Sakaguchi flask (volume 500 ml) and autoclaved at 120° C. for 15 minutes. To the flask, there was added seed culture (10 ml) which was obtained by previously cultivating the strain in the same medium with shaking at 30° C. for 1 day. The flask was incubated on a shaker at 30° C. for 3 days.

After completion of cultivation, the culture medium was collected and centrifuged to remove microbial cells. Hydrochloric acid was added to the resulting supernatant to adjust pH thereof to 3. The precipitate thus formed was filtered off, thoroughly washed with water and dried to obtain 12α-hydroxypregna-1,4-dien-3-one-20α-carboxylic acid (950 mg).

A small portion of 12α-hydroxypregna-1,4-dien-3-one-20α-carboxylic acid thus obtained was dissolved in methanol in the concentration of 1% and the solution (10 μl) was injected to a high-performance liquid chromatography apparatus equipped with a μBondapak C-18 column (HLC-GPC-244 type manufactured by Waters Associates in U.S.A.). The column was eluted with water-methanol (25:75, v/v, pH 4.0) at the rate of 1 ml/min. and refractive index of the eluate was measured. The area ratio of each peaks of the chromatogram thus obtained was measured by using a planimeter (Shimadzu Chromatopack C-RIA manufactured by Shimadzu Corporation in Japan). The area ratio showed that the purity of 12α-hydroxypregna-1,4-dien-3-one-20α-carboxylic acid was 93%.

The compound corresponding to the main peak of the chromatogram was isolated by thin layer chromatography and identified as 12α-hydroxypregna-1,4-dien-3-one-20α-carboxylic acid.

Mass spectrum: m/z=358 [M]$^+$; 340 [M—H$_2$O]$^+$; and 322 [M—2H$_2$O]$^+$. The presence of 3-keto-1,4-dien was confirmed by m/z=122 and the presence of —CH(CH$_3$)COOH was confirmed by m/z=74.

NMR spectrum (90 MHz): $\delta_{HMS}^{DMSO-d6}$=0.65 (3H, s) 18-CH$_3$; 1.05 (3H, d) 21-CH$_3$; 1.13 (3H, s) 19-CH$_3$; 3.74 (1H, t, J=3 Hz) 12β-H; 4.33 (1H, d) 12α-OH; 5.93 (1H, s) 4-H; 6.06 (1H, d, J=10 Hz) 2-H; and 7.08 (1H, d, J=10 Hz) 1-H.

EXAMPLE 5

*Alcaligenes faecalis* D4020-H405 strain was cultivated as follows:

Composition of culture medium

| | |
|---|---|
| Deoxycholic acid | 4.0 g |
| Ammonium nitrate | 0.2 g |
| Potassium dihydrogen phosphate | 0.12 g |
| Dipotassium hydrogen phosphate | 0.61 g |
| Magnesium sulfate heptahydrate | 0.02 g |
| Yeast extract | 0.02 g |
| Glucose | 0.1 g |
| Sodium hydroxide | 0.4 g |
| Tap water | to 100 ml |

The above ingredients were admixed to obtain a culture medium (pH 8.4, 100 ml). The medium was placed in a Sakaguchi flask (volume 500 ml) and autoclaved at 120° C. for 15 minutes. To the flask, there was added seed culture (10 ml) which was obtained by previously cultivating the strain in the same medium with shaking at 30° C. for 1 day. The flask was incubated on a shaker at 30° C. for 5 days.

After completion of cultivation, the culture medium was collected and centrifuged to remove microbial cells. Hydrochloric acid was added to the resulting supernatant to adjust pH thereof to 3. The precipitate thus formed was filtered off, thoroughly washed with water and dried to obtain 12α-hydroxypregna-1,4-dien-3-one-20α-carboxylic acid (3.2 g).

When the purity of 12α-hydroxypregna-1,4-dien-3-one-20α-carboxylic acid was determined according to the same procedure as in Example 4, it was 97%.

EXAMPLE 6

By using *Alcaligenes faecalis* D4020-H405 strain, the same procedure as described in Example 5 was repeated except that the concentration of deoxycholic acid was varied and sodium hydroxide was formulated in an amount of 1/10 time as much as that of deoxycholic acid to be used and that the incubation period was varied to determine the yield of oxidation products of deoxycholic acid and the amount of unreacted deoxycholic acid at various concentrations of the substrate.

The results are shown in Table 4.

TABLE 4

| Compounds | Yield or amount (g) Substrate concentration and Incubation period | | | | |
| --- | --- | --- | --- | --- | --- |
| | 2 g/l 1 day | 5 g/l 2 days | 10 g/l 3 days | 30 g/l 5 days | 50 g/l 5 days |
| 12α-hydroxypregna-1,4-dien-3-one-20α-carboxylic acid | 1.5 | 3.76 | 7.9 | 21.1 | 39.6 |
| other oxidation products of deoxycholic acid | 0.1 | 0.24 | 0.4 | 2.1 | 0.8 |
| unreacted deoxycholic acid | — | — | trace | 1.9 | 1.1 |

What is claimed is:

1. A microbial process for producing 12α-hydroxypregna-1,4-dien-3-one-20α-carboxylic acid or a salt thereof, which comprises cultivating a strain of *Pseudomonas arvilla* D-235 (FERM BP-181) or a strain of *Alcaligines faecalis* D4040 (FERM BP-182) or its mutant, capable of producing 12α-hydroxypregna-1,4-dien-3-one-20α-carboxylic acid or a salt thereof by utilizing deoxycholic acid or a salt thereof as a substrate, in a culture medium containing said substrate, and collecting the resulting compound.

2. A microbial process according to claim 1, wherein the microbe is *Alcaligenes faecalis* D4020 strain (FERM BP-182).

3. A microbial process according to claim 1, wherein the microbe is *Alcaligenes faecalis* D4020-H405 strain (FERM BP-183).

4. A microbial process according to claim 1, 2, or 3, wherein the cultivation is carried out under an aerobic condition by using the medium containing the substrate in an amount of about 1 to 200 g/l as deoxycholic acid.

* * * * *